United States Patent [19]
Andrews

[11] Patent Number: 5,842,857
[45] Date of Patent: Dec. 1, 1998

[54] CADDY FOR A DENTAL ARTICULATOR

[76] Inventor: Lawrence F. Andrews, 6101 La Jolla Mesa Dr., La Jolla, Calif. 92037

[21] Appl. No.: 94,527

[22] Filed: Jun. 12, 1998

[51] Int. Cl.$^6$ .................................................. A61C 119/00
[52] U.S. Cl. .............................. 433/60; 433/59; 433/34; 433/58; 433/37
[58] Field of Search .................. 433/34, 37, 48, 433/60, 214, 213, 59, 58

[56] References Cited

U.S. PATENT DOCUMENTS

| | | | |
|---|---|---|---|
| 3,908,271 | 9/1975 | Derda et al. | 433/6 |
| 4,543,062 | 9/1985 | Lee | 433/71 |
| 4,854,868 | 8/1989 | Pitre | 433/60 |
| 5,044,949 | 9/1991 | Xanthopoulos | 433/58 |
| 5,154,609 | 10/1992 | George | 433/68 |
| 5,176,515 | 1/1993 | Andrews | 433/24 |
| 5,366,373 | 11/1994 | Mumolo et al. | 433/58 |
| 5,622,497 | 4/1997 | Cho | 433/60 |

*Primary Examiner*—Gene Mancene
*Assistant Examiner*—Pedro Philogene
*Attorney, Agent, or Firm*—Gray Cary Ware & Freidenrich

[57] ABSTRACT

A caddy is provided for either permanent or removable attachment to a dental articulator for retaining one or more bite registrations at or near the dental articulator.

28 Claims, 3 Drawing Sheets

CADDY FOR A DENTAL ARTICULATOR

BACKGROUND OF THE INVENTION

The invention is a caddy for a dental articulator that holds one or more bite registrations. More particularly, the invention concerns a caddy that may be detachably mounted on a dental articulator to conveniently retain one or more bite registrations at or near the articulator.

Orthodontists use dental casts mounted on dental articulators to determine relative positions of the teeth and jaws of a patient. A bite registration is used to align dental casts for mounting on an articulator. Should a cast come loose from the articulator, the bite registration will be needed to realign and remount the cast. For such a possibility it is customary for the bite registration to be stored between the teeth of the mounted dental casts. This way is less likely to get lost, distorted, or broken. However, most of the time, a bite registration is an inconvenience because, whenever the articulator is used to examine a tooth, the bite, or the arch shape, the bite registration must be temporarily removed, set aside, and, after use, replaced. During this time the bite registration is susceptible to being lost, distorted, or broken.

Accordingly, for convenience and for saving time and cost, it would be desirable to be able to retain and protect a bite registration at or near an articulator while not located between dental casts.

SUMMARY OF THE INVENTION

The invention is based on the critical realization that the structure of an articulator provides the opportunity for supporting a caddy—a small container—for holding a bite registration. The inventor has further realized that it would be very convenient if the caddy were mounted to the articulator in order to have it be an auxiliary device for optional use. Finally, the inventor has provided for detachably mounting the caddy to the articulator in such a way as not to interfere with viewing of the dental casts.

Accordingly, it is an objective of this invention to provide for the convenient storing of a bite registration at or near a dental articulator instead of between dental casts mounted on the articulator.

A further objective is to provide for such retention by means of a caddy on the articulator.

A still further objective is to make such a caddy removable from the articulator.

Other advantages and objectives of this invention will be manifest from the following description when read with reference to the accompanying drawings.

DETAILED DESCRIPTION OF THE PREFERRED EMBODIMENTS

Figure 1:
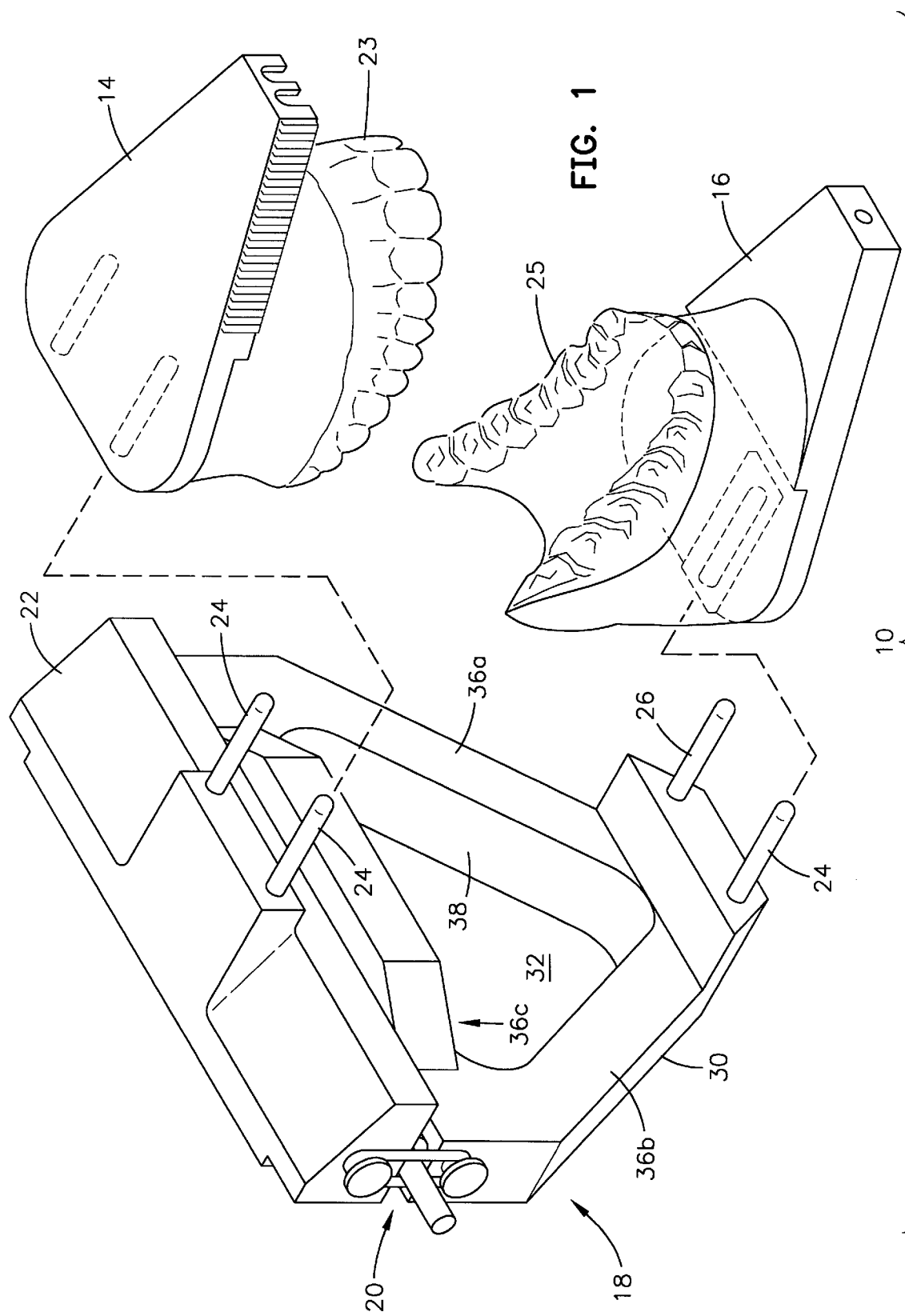
FIG. 1 is a partially exploded perspective view of a dental articulator embodied as an occlusofacial simulator.

U.S. Pat. No. 5,176,515 to the inventor, which is incorporated herein by reference, describes an occlusofacial simulator, which is a type of dental articulator. FIG. 1 illustrates elements of such an occlusofacial simulator 10. These elements include an upper cast support member 14 and a lower cast support member 16. The upper and lower cast support members 14 and 16 are mounted to a frame 18 that has simulated temporomandibularjoints (TMJs), one of which is indicated by reference numeral 20. An upper member 22 is hingedly connected to the simulated TMJs 20. The upper and lower cast support members 14 and 16 are received on respective pairs of parallel posts 24 and 26 of the frame 18. When they are received on the posts, the upper and lower cast support members 14 and 16 are mounted to the frame 18. When assembled as just described, the upper cast support member 14 and the upper member 22 together simulate a transverse section of the cranial base of a human skull to which a maxillary dental cast 23 can be mounted in the same orientation to the TMJs as the patient. The lower cast support member 16 of the occlusofacial simulator 10 simulates the mandible and supports a mandibular dental cast 25. The mandibular cast is aligned with the maxillary cast with a sheet of wax into which the patient has bitten, leaving indentations. This sheet of wax is the "bite registration" that the caddy holds.

As clearly seen in FIG. 1, the frame 18 includes a primary frame piece 30 that, in plan, exhibits a triangularly-shaped open center portion 32 that is bounded by frame sides 36a, 36b, and 36c. The frame sides define a triangularly-shaped periphery surface 38.

Figure 2:
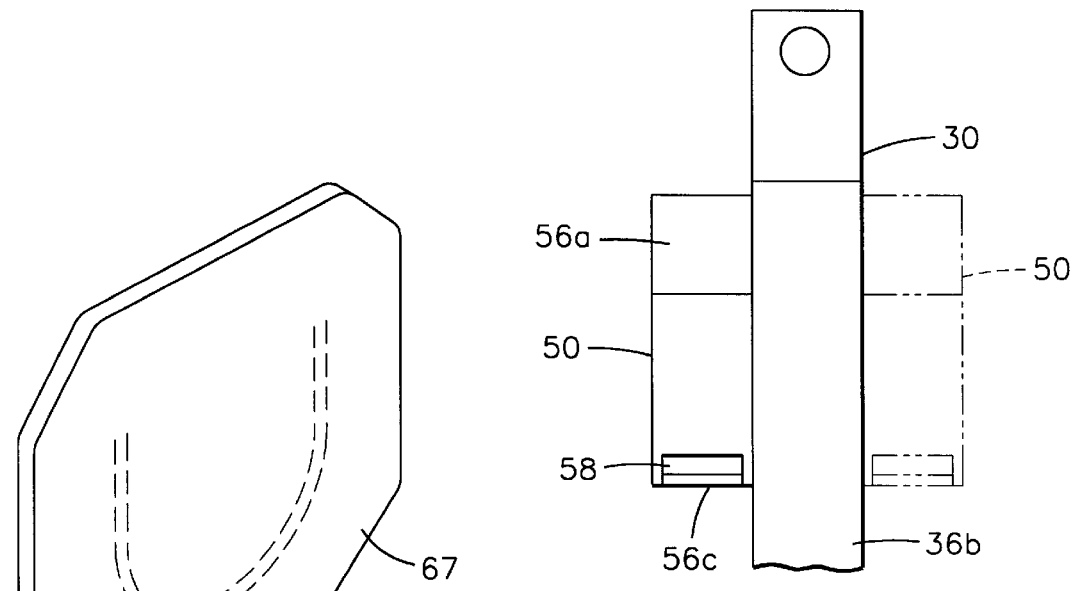
FIG. 2 is a partial side elevation showing a caddy mounted to an element of the occlusofacial simulator of FIG. 1.
Figure 3:
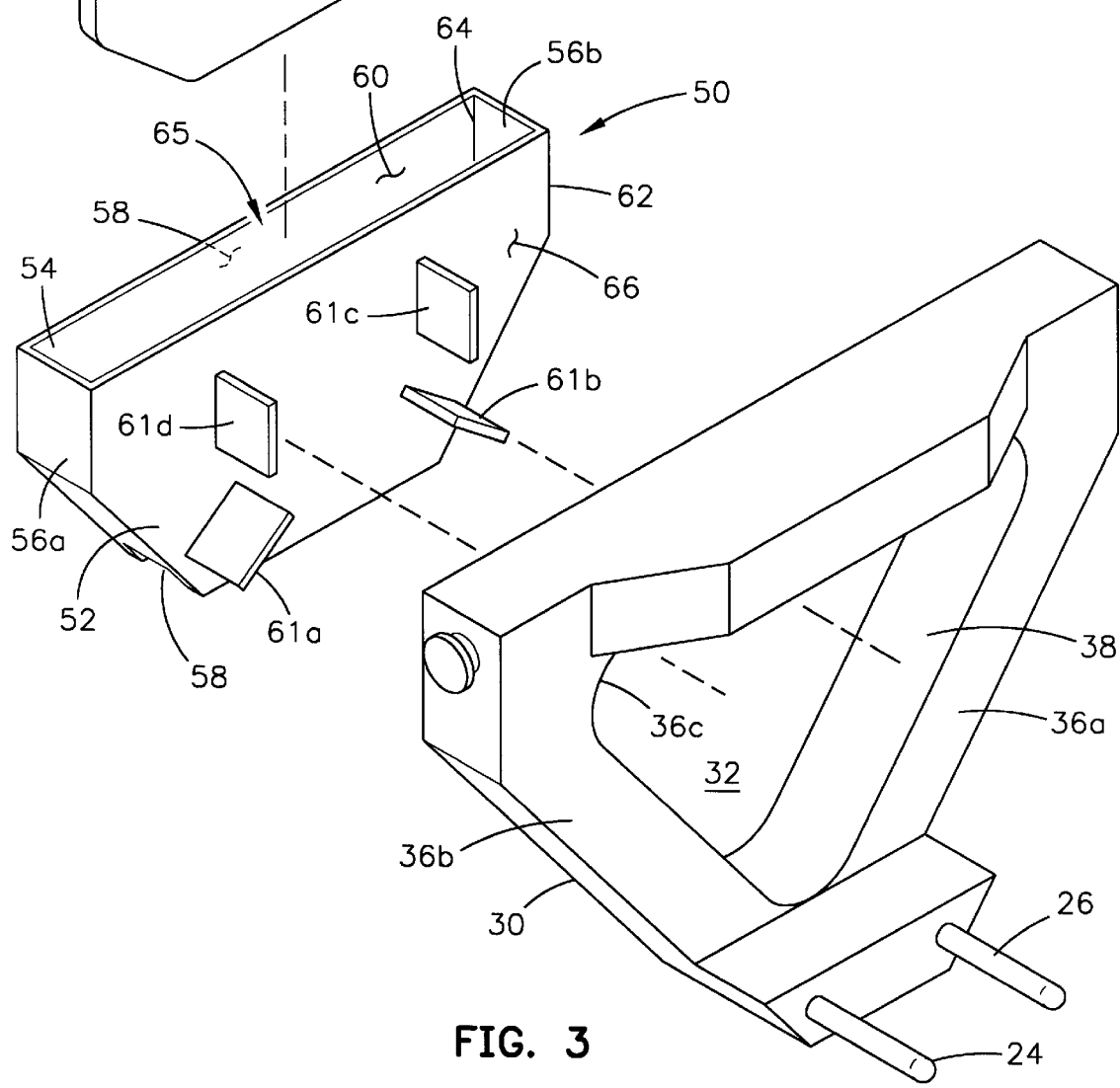
FIG. 3 is an exploded perspective view of the caddy positioned with respect to a first side of the occlusofacial simulator element.

Refer now to FIGS. 2 and 3 where a caddy 50 is shown in combination with the frame 30. The caddy 50 is mounted on the outside of the frame 30, such that the frame 30 is sandwiched between the caddy 50 and the posts 24 and 26. The caddy 50 includes a pair of spaced-apart, generally planar, generally polygonally-shaped members, each preferably made of plastic material. Reference numeral 52 refers to a first of the two members, while reference numeral 54 refers to a second of the two members. Each of the members 52, 54 may be in the shape of a six-sided polygon although this is not critical to the invention. In fact the shape can be any that is useful or appropriate. Spacers 56a, 56b, and 56c are attached to opposing surfaces 66 and 60 of the first and second members, at or near the peripheries 62, 64 of the opposing surfaces in order to form a caddy space 65 that receives and retains one or more bite registrations. A bite registration 67 is shown positioned for receipt in the caddy space 65. On an attachment surface 66 of the first member 52 that is oppositely-directed to the surface 58 of the first member 52 to which the spacers are mounted, a retainer comprising one or more retention structures, is mounted. In the preferred embodiment shown in FIG. 3, there are a plurality of retention structures 61a–61d, each comprising a generally rectangular panel, mounted upright, on a narrow edge, to the attachment surface of the first member 52 to be generally perpendicular thereto. These panels are preferably made of a somewhat flexible plastic material and are mounted on the mounting surface of the first member 52 such that, for each panel, an edge engages the peripheral surface 38 when the caddy 50 is brought to a close abutting relationship with the primary frame piece 30. The flexibility of the panels, and their close proximity to the peripheral surface 38, retain the caddy 50 on the primary frame member 30, but permit the caddy 50 to be detached therefrom and reattached, as needed or desired.

Figure 4:
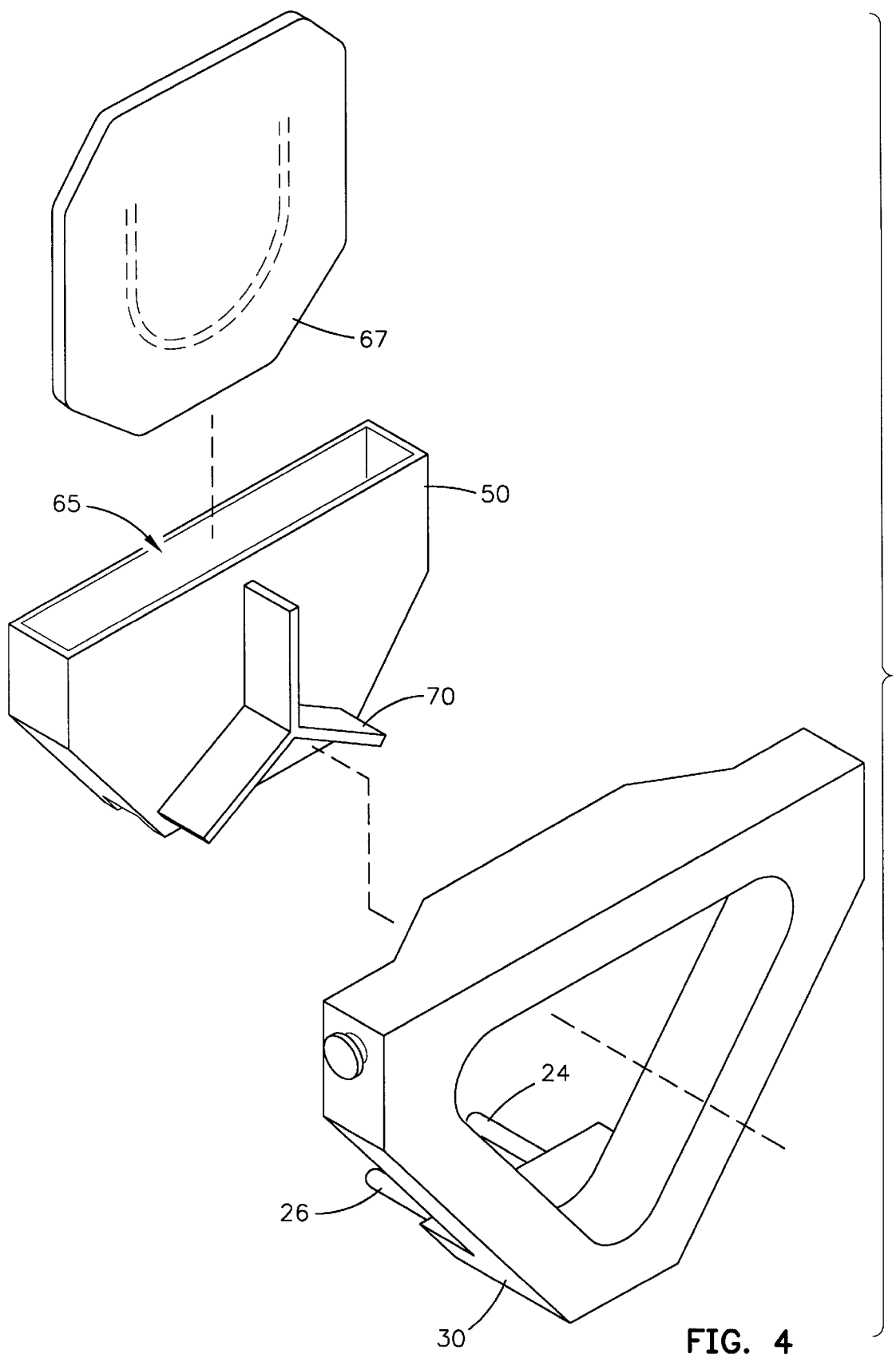
FIG. 4 is an illustration of the shape of an alternate retainer for the caddy of FIGS. 2 and 3.

For retention of the caddy on the occlusofacial simulator of FIG. 1, alternate retainers are conceivable. For example, a 3-legged retainer 70 such as is illustrated in FIG. 4 may be used. Other retainers that permit detachably mounting the caddy 50 would include, without limit, snaps, hook-and-eye material, brackets, loops, hooks, magnets and equivalent mechanisms. Moreover as shown in FIGS. 2 and 4, the caddy 50 may be mounted on the inside of the frame 30, just above the posts 24 and 26. Further, if desired, the caddy can be permanently attached to the occlusofacial simulator 10. Additionally, a caddy can be attached-permanently or removably— to any dental articulator for retention of one or more bite registrations at or near the articulator. Moreover, more than one caddy can be permanently or detachably mounted, each for retaining one or more bite registrations at or near a dental articulator.

Furthermore, the function of the retainer is to act between the caddy and the articulator to retain the caddy to or on the articulator. Thus, the retainer may be wholly on the articulator, or may have elements distributed between the articulator and the caddy.

When describing an element of the invention in the singular, the plural is contemplated, unless limitation to the singular is explicitly stated.

This invention may be practiced according to the disclosed embodiment. However, the embodiment is merely exemplary and many modifications and variations can be made to it without departing from the spirit of this invention, as defined in the following claims.

I claim:

1. A dental apparatus, comprising:
    a caddy for holding one or more bite registrations; and
    a retainer on the caddy for engaging a dental articulator.
2. The dental apparatus of claim 1, wherein the caddy includes:
    two spaced-apart, generally planar, generally polygonal members; and
    one or more spacers attached to opposing surfaces of the two members.
3. The dental apparatus of claim 2, wherein each of the members is a planar, six-sided material sheet.
4. The dental apparatus of claim 3, wherein the one or more spacers are located near corresponding peripheries of the opposing surfaces.
5. The dental apparatus of claim 1, wherein the caddy includes an attachment surface, and the retainer includes a plurality of rectangular panels mounted upright on the attachment surface.
6. The dental apparatus of claim 5, wherein:
    the caddy includes:
        two spaced-apart, generally planar, generally polygonal members, each member having two oppositely-directed surfaces; and
        one or more spacers attached to opposing surfaces of the two members;
    and, the retainer includes a plurality of panels mounted upright on a surface of a first member that is oppositely-directed to the surface of the first member to which the one or more spacers are attached.
7. The dental apparatus of claim 6, wherein each of the members is a planar, six-sided material sheet.
8. The dental apparatus of claim 7, wherein the one or more spacers are located near corresponding peripheries of the opposing surfaces.
9. A dental apparatus, comprising:
    a dental articulator; and
    a bite registration caddy mounted on the articulator.
10. The dental apparatus of claim 9, further including:
    a retainer acting between the dental articulator and the caddy for retaining the caddy to the dental articulator.
11. The dental apparatus of claim 9, wherein the retainer is on the caddy.
12. The dental apparatus of claim 11, wherein the caddy includes:
    two spaced-apart, generally planar, generally polygonal members; and
    one or more spacers attached to opposing surfaces of the two members.
13. The dental apparatus of claim 12, wherein each of the members is a planar, six-sided material sheet.
14. The dental apparatus of claim 13, wherein the one or more spacers are located near corresponding peripheries of the opposing surfaces.
15. The dental apparatus of claim 11, wherein the caddy includes an attachment surface, and the retainer includes a plurality of rectangular panels mounted upright on the attachment surface.
16. The dental apparatus of claim 15, wherein:
    the caddy includes:
        two spaced-apart, generally planar, generally polygonal members, each member having two oppositely-directed surfaces; and
        one or more spacers attached to opposing surfaces of the two members;
    and, the retainer includes a plurality of panels mounted upright on a surface of a first member that is oppositely-directed to the surface of the first member to which the one or more spacers are attached.
17. The dental apparatus of claim 16, wherein each of the members is a planar, six-sided material sheet.
18. The dental apparatus of claim 17, wherein the one or more spacers are located near corresponding peripheries of the opposing surfaces.
19. The dental apparatus of claim 9, wherein the dental articulator is an occlusofacial simulator.
20. The dental apparatus of claim 19, wherein the occlusofacial simulator includes a frame with a triangular opening, further including a retainer acting between the opening and the caddy for retaining the caddy on the frame.
21. The dental apparatus of claim 20, wherein the retainer is on the caddy.
22. The dental apparatus of claim 21, wherein the caddy includes:
    two spaced-apart, generally planar, generally polygonal members; and
    one or more spacers attached to opposing surfaces of the two members.
23. The dental apparatus of claim 22, wherein each of the members is a planar, six-sided material sheet.
24. The dental apparatus of claim 23, wherein the one or more spacers are located near corresponding peripheries of the opposing surfaces.
25. The dental apparatus of claim 21, wherein the caddy includes an attachment surface, and the retainer includes a plurality of rectangular panels mounted upright on the attachment surface.
26. The dental apparatus of claim 25, wherein:
    the bite registration caddy includes:
        two spaced-apart, generally planar, generally polygonal members, each member having two oppositely-directed surfaces; and
        one or more spacers attached to opposing surfaces of the two members;
    and, the retainer includes a plurality of panels mounted upright on a surface of a first member that is oppositely-directed to the surface of the first member to which the one or more spacers are attached.
27. The dental apparatus of claim 26, wherein each of the members is a planar, six-sided material sheet.
28. The dental apparatus of claim 27, wherein the one or more spacers are located near corresponding peripheries of the opposing surfaces.

* * * * *